United States Patent
Simpson et al.

(10) Patent No.: US 10,478,231 B2
(45) Date of Patent: Nov. 19, 2019

(54) SPINAL IMPLANT SYSTEM AND METHOD

(71) Applicant: WARSAW ORTHOPEDIC, INC, Warsaw, IN (US)

(72) Inventors: Joshua W. Simpson, Collierville, TN (US); Gary S. Lindemann, Collierville, TN (US); Jason M. May, Collierville, TN (US); Maria-Rosa Padilla, Nesbit, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 43 days.

(21) Appl. No.: 15/850,980

(22) Filed: Dec. 21, 2017

(65) Prior Publication Data

US 2018/0132906 A1 May 17, 2018

Related U.S. Application Data

(63) Continuation of application No. 14/864,482, filed on Sep. 24, 2015, now Pat. No. 9,924,976.

(51) Int. Cl.
*A61B 17/70* (2006.01)
(52) U.S. Cl.
CPC .................. *A61B 17/7053* (2013.01)
(58) Field of Classification Search
CPC .................................................. A61B 17/7053
See application file for complete search history.

(56) References Cited

U.S. PATENT DOCUMENTS

| | | | |
|---|---|---|---|
| 5,356,412 | A | 10/1994 | Golds et al. |
| 6,277,120 | B1 | 8/2001 | Lawson |
| 7,166,108 | B2 | 1/2007 | Mazda et al. |
| 7,481,828 | B2 | 1/2009 | Mazda et al. |
| 7,959,654 | B2 | 6/2011 | Mazda et al. |
| 8,162,946 | B2 | 4/2012 | Baccelli et al. |
| 8,172,843 | B2 | 5/2012 | Baccelli et al. |
| 8,870,870 | B2 | 10/2014 | Baccelli et al. |
| 8,926,668 | B2 | 1/2015 | Douget |
| 8,936,625 | B2 | 1/2015 | Larroque-Lahitette et al. |
| 2005/0131404 | A1 | 6/2005 | Mazda et al. |
| 2010/0249845 | A1 | 9/2010 | Meunier et al. |
| 2011/0106179 | A1 | 5/2011 | Prevost et al. |

(Continued)

FOREIGN PATENT DOCUMENTS

| | | |
|---|---|---|
| EP | 1926444 A1 | 6/2008 |
| EP | 2052689 A1 | 4/2009 |

(Continued)

OTHER PUBLICATIONS

European Search Report for EP16849749.3 date of completion is Apr. 17, 2019 (8 pages).

(Continued)

*Primary Examiner* — Ellen C Hammond

(57) ABSTRACT

A spinal implant comprises a body including an inner surface that defines a cavity configured for disposal of a member. A locking element is engageable with the member within the cavity to fix the member with the body. The body further includes a wall that defines a bay configured for disposal of a longitudinal element being engageable with the wall to fix the longitudinal element with the body independent of the member. Systems and methods are disclosed.

20 Claims, 7 Drawing Sheets

(56) References Cited

U.S. PATENT DOCUMENTS

| | | |
|---|---|---|
| 2011/0301644 A1 | 12/2011 | Belliard |
| 2012/0130373 A1 | 5/2012 | Larroque-Lahitette |
| 2012/0150232 A1 | 6/2012 | Van Nortwick et al. |
| 2012/0271354 A1 | 10/2012 | Baccelli et al. |
| 2012/0303121 A1 | 11/2012 | Douget et al. |
| 2013/0023878 A1 | 1/2013 | Belliard et al. |
| 2013/0304136 A1 | 11/2013 | Gourlaouen-Preissler et al. |
| 2014/0066987 A1 | 3/2014 | Hestad et al. |
| 2014/0094850 A1 | 4/2014 | Clement et al. |
| 2014/0257397 A1* | 9/2014 | Akbarnia ............ A61B 17/8869 606/263 |
| 2014/0257400 A1 | 9/2014 | Gourlaougen-Preissler et al. |

FOREIGN PATENT DOCUMENTS

| | | |
|---|---|---|
| EP | 2184023 A1 | 5/2010 |
| EP | 2184023 A1 | 12/2010 |
| EP | 2052689 B1 | 12/2011 |
| EP | 1926444 B1 | 3/2012 |
| EP | 2521500 A1 | 11/2012 |
| EP | 2668921 A1 | 12/2013 |
| EP | 2521500 B1 | 3/2014 |
| EP | 1926444 B2 | 12/2014 |
| EP | 2668921 B1 | 12/2015 |
| FR | 2842724 A1 | 7/2002 |
| FR | 2842724 A1 | 1/2004 |
| FR | 2890849 A1 | 9/2005 |
| FR | 2890849 A1 | 3/2007 |
| WO | 2007034112 A1 | 3/2007 |

OTHER PUBLICATIONS

International Search Report for PCT/US2016/053441 date of completion is Dec. 16, 2016 (2 pages).

* cited by examiner

SPINAL IMPLANT SYSTEM AND METHOD

CROSS-REFERENCE TO RELATED APPLICATIONS

This application is a continuation of application U.S. patent application Ser. No. 14/466,454, filed on Aug. 22, 2014, which is hereby incorporated by reference herein, in its entirety.

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants, such as vertebral rods, bone screws and sub-laminar wire, for stabilization of a treated section of a spine. This disclosure describes an improvement over these prior technologies.

SUMMARY

In one embodiment, a spinal implant comprises a body including an inner surface that defines a cavity configured for disposal of a member. A locking element is engageable with the member within the cavity to fix the member with the body. The body further includes a wall that defines a bay configured for disposal of a longitudinal element being engageable with the wall to fix the longitudinal element with the body independent of the member. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
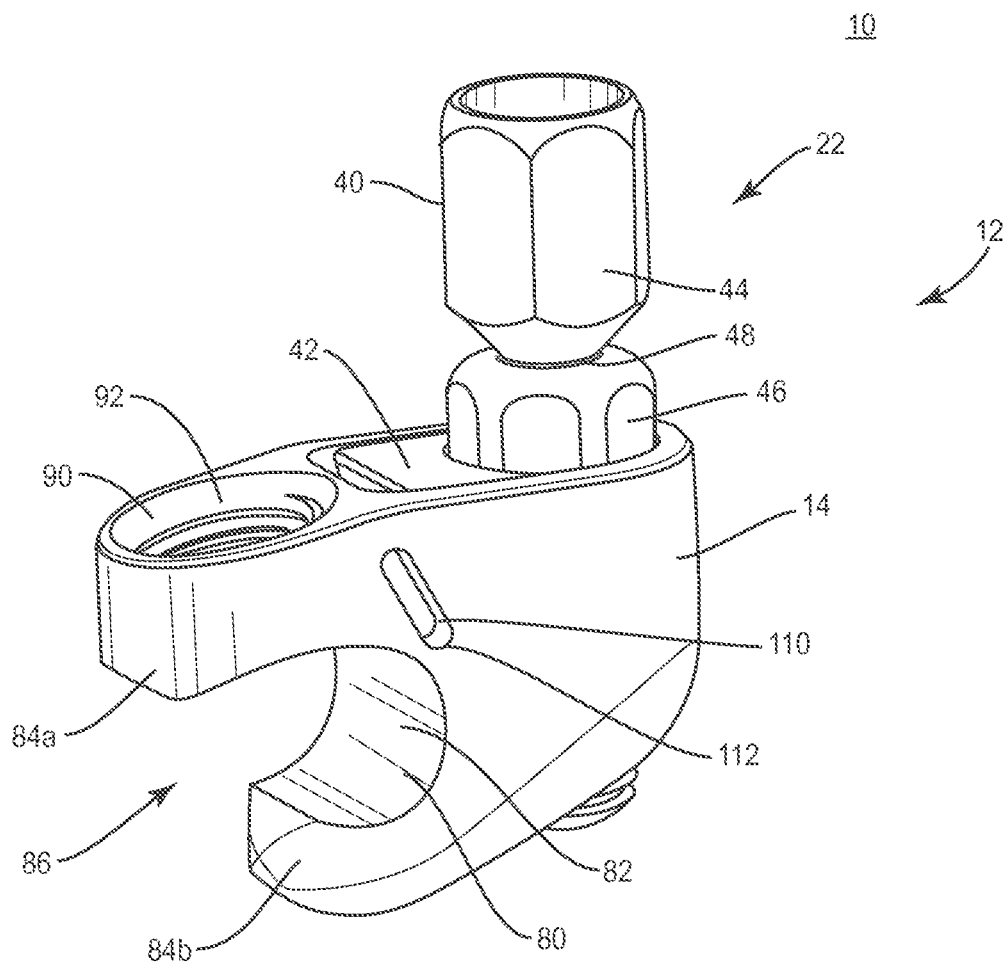
FIG. 1 is a perspective view of one embodiment of components of a surgical system in accordance with the principles of the present disclosure.
Figure 2:
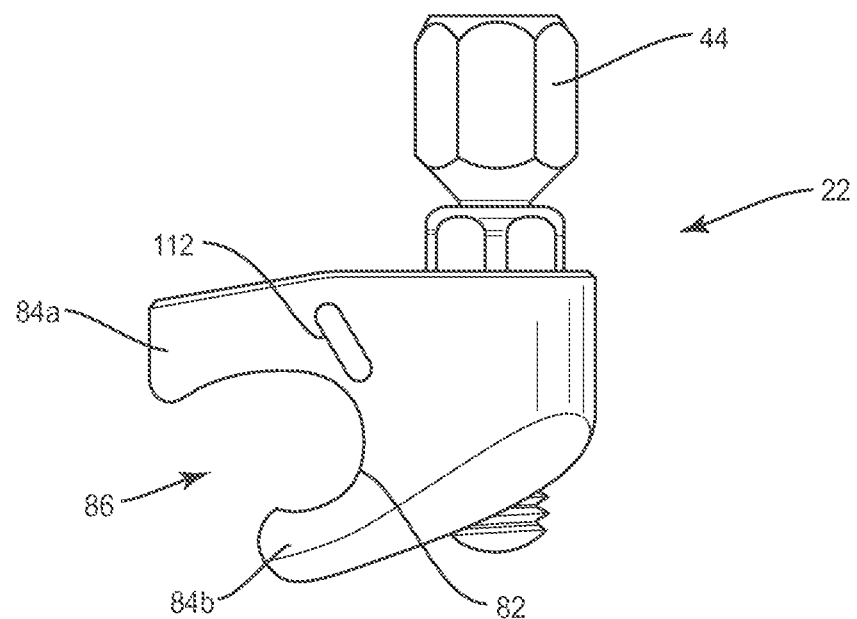
FIG. 2 is a side view of the components shown in FIG. 1.
Figure 3:
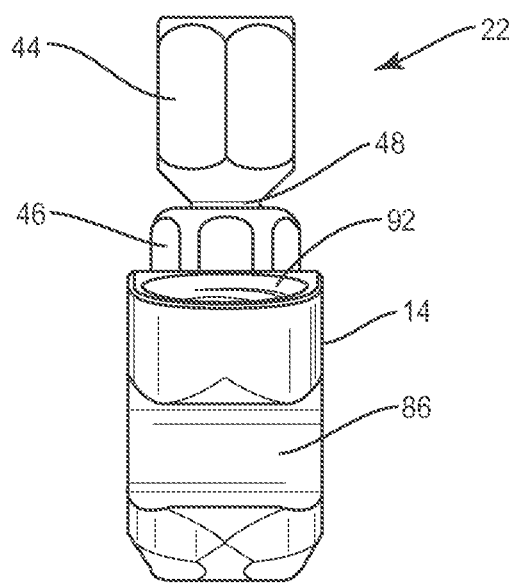
FIG. 3 is a side view of the components shown in FIG. 1.
Figure 4:
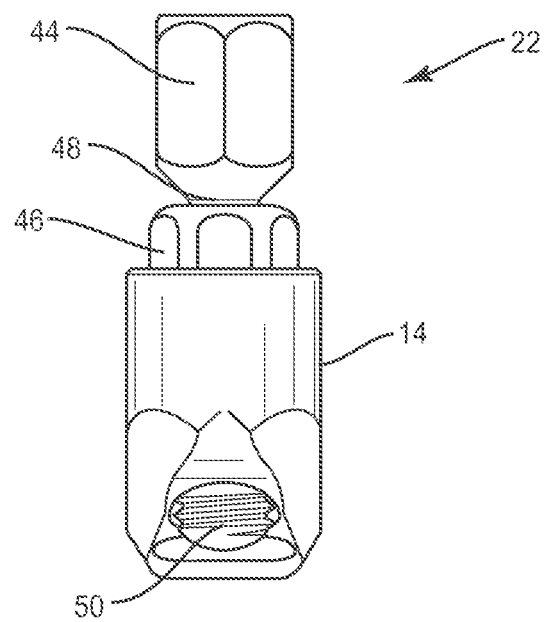
FIG. 4 is a side view of the components shown in FIG. 1.
Figure 5:
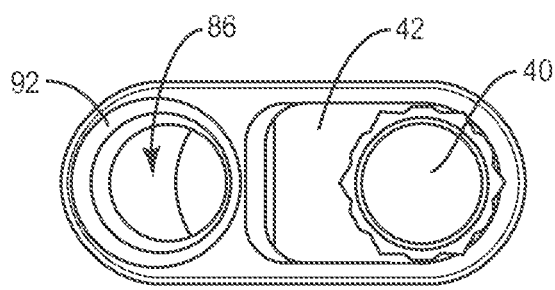
FIG. 5 is an end view of the components shown in FIG. 1.
Figure 6:
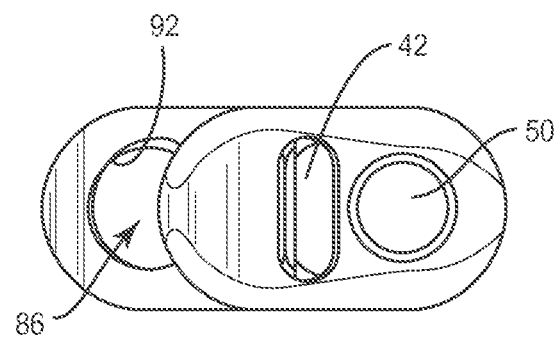
FIG. 6 is an end view of the components shown in FIG. 1.

The exemplary embodiments of a surgical system and related methods of use are discussed in terms of medical devices for the treatment of musculoskeletal disorders and more particularly, in terms of a surgical system and method for correction of a spine disorder. In some embodiments, the surgical system may be employed in applications for correction of deformities, such as scoliosis and kyphosis.

In some embodiments, the surgical system includes a spinal implant including a tether connector. In some embodiments, the surgical system includes a spinal implant including a tether connector configured to fix a posterior spinal rod to a spine by a tether such that the spinal rod is fixed in a flexible and/or dynamic configuration. In some embodiments, the tether connector is fixed with a spine at a top level of a spinal construct. In some embodiments, the tether connector is fixed with a spine at one or a plurality of levels of a spinal construct. In some embodiments, the tether connector is fixed to a spinal rod and maintains a tether in place after the tether is wrapped about vertebral tissue, such as, for example, a lamina. In some embodiments, the tether connector includes one or a plurality of coupling members, such as, for example, set screws. In some embodiments, the tether connector includes a set screw that engages a spinal rod and a set screw that facilitates locking of a tether.

In some embodiments, the tether connector includes one or a plurality of coupling members, such as, for example, set screws that attach a sub-laminar tether to a spinal rod. In some embodiments, the tether connector includes two set screws that allow for locking of a spinal rod and a tether separately. In some embodiments, the tether connector provides separate manipulation of the spinal rod and the tether during surgery. In some embodiments, the tether connector includes a set screw that facilitates locking of a tether, the set screw including a locking portion, such as, for example, a break off element and a revision portion. In some embodiments, the break off element is offset from the revision portion.

In some embodiments, the tether connector includes a lock, such as, for example, a locking cleat that facilitates attachment of a sub-laminar tether to a spinal rod. In some embodiments, the locking cleat includes fixation elements, such as, for example, teeth that maximize the surface area holding the tether with the teeth. In some embodiments, the locking cleat includes teeth that maximize line to line pressure and increase frictional engagement with the tether. In some embodiments, the locking cleat includes teeth having a serpentine configuration and/or define a serpentine path therebetween to increase frictional engagement with the tether. In some embodiments, the set screw connected with the locking cleat has a break off element to provide a positive indicator that the tether connector is selectively secured with vertebral tissue. In some embodiments, the tether connector includes a locking cleat connected with a set screw such that the screw is rotated to translate the cleat. In some embodiments, the cleat is translated to define a pathway of the tether connector for disposal of a tether. In some embodiments, the cleat is translated between a first position relative to the tether connector to define a pathway of the tether connector for disposal of a tether and a second position relative to the tether connector such that the cleat is clamped to the tether to fix the tether with the tether connector. In some embodiments, the cleat is connected with the set screw via a pin.

In some embodiments, the tether connector includes a threaded opening for disposal of a set screw engageable with a spinal rod, a break off tether locking set screw, a surface defining a spinal rod slot, a tether locking cleat and a surface defining surgical instrument attachment slots. In some embodiments, the tether connector has a minimized profile. In some embodiments, the tether connector has a 9 millimeter (mm) profile and/or run along a spinal rod.

In some embodiments, the surgical system is used with surgical navigation, such as, for example, fluoroscope or image guidance. In some embodiments, one or all of the components of the surgical system are disposable, peel-pack, pre-packed sterile devices. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone, supine position, lateral and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an", and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to exemplary embodiments of the present disclosure, which are illustrated in the accompanying figures. Turning to FIGS. 1-6, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TOP), HA-TOP, calcium sulfate, or other resorbable polymers such as polypeptide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Figure 7:
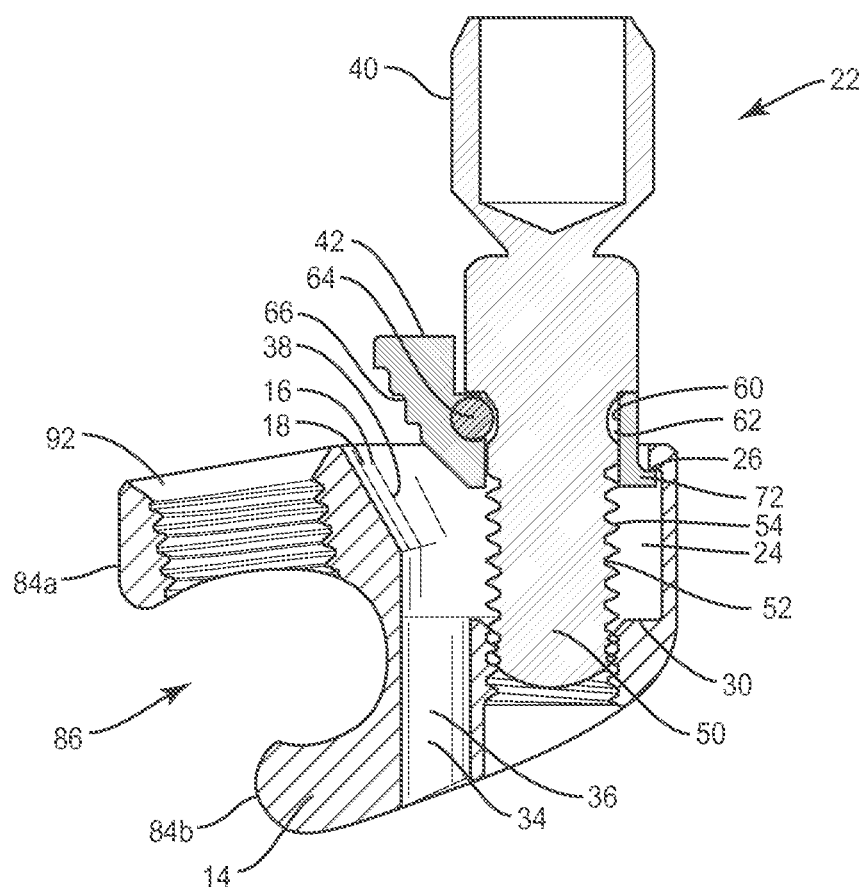
FIG. 7 is a cross section view of one embodiment of components of a surgical system in accordance with the principles of the present disclosure.
Figure 8:
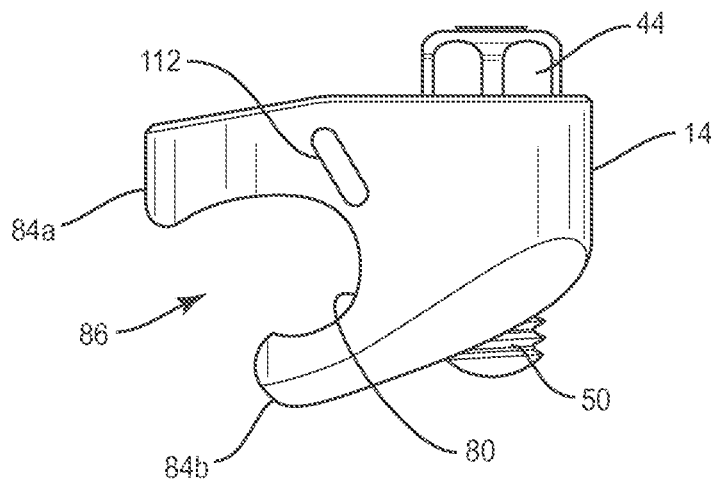
FIG. 8 is a side view of one embodiment of components of a surgical system in accordance with the principles of the present disclosure.
Figure 9:
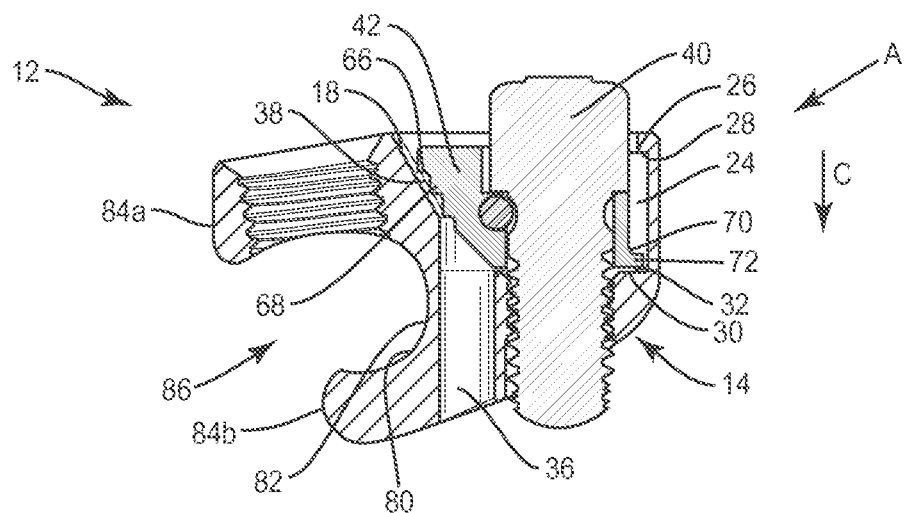
FIG. 9 is a cross section view of the components shown in FIG. 8.

Spinal implant system 10 comprises a spinal implant, such as, for, example, a connector 12. Connector 12 includes a body 14 having a surface 16 that defines a cavity 18 configured for disposal of a member, such as, for example, a tether 20, as described herein. Cavity 18 is configured for movable disposal of a locking element 22 configured to fix tether 20 with body 14 between a non-locking orientation, such as, for example, as shown in FIG. 7, and a locked orientation, such as, for example, as shown in FIG. 9 and described herein. In some embodiments, cavity 18 may have various cross section configurations, such as, for example, oval, oblong, triangular, rectangular, square, polygonal, irregular, uniform, non-uniform, variable and/or tapered. In some embodiments, surface 16 may include gripping elements or surfaces, such as, for example, rough, arcuate, undulating, mesh, porous, semi-porous, dimpled and/or textured to facilitate engagement with tether 20.

Surface 16 defines a slot 24 configured for engagement with a portion of locking element 22, as described herein. Slot 24 includes a proximal end 26 having a surface 28 and a distal end 30 having a surface 32. Ends 26, 30 define a range of translation of locking element 22 as locking element 22 translates within cavity 18 between a non-locking orientation and a locked orientation.

Surface 16 defines a channel 34 in communication with cavity 18. Channel 34 is configured for disposal of tether 20. In some embodiments, channel 34 includes a linear portion 36 and a transverse portion 38. Tether 20 is configured for disposal with channel 34 between a movable configuration and a fixed configuration, as described herein. Transverse portion 38 defines an engagement surface and/or a lock surface such that tether 20 is fixed with transverse portion 38 via compressive forces and/or friction forces, applied at least in the direction shown by arrow A in FIG. 9, by locking element 22, as described herein. In some embodiments, the compressive forces applied by locking element 22, to tether 20, and/or to transverse portion 38 may be directed in various orientations, such as, for example, perpendicular, transverse and/or at angular orientations, such as acute or obtuse.

Locking element 22 includes a screw 40 and a fixation element, such as, for example, a cleat 42. Screw 40 includes a portion 44 and a portion 46. Portions 44, 46 are connected at a reduced diameter portion 48 that is tangibly connected to portion 46. In some embodiments, portion 46 is configured for a threaded engagement with surface 16. In some embodiments, portions 44, 46 are fabricated from a fracturing and/or frangible material such that manipulation of portion 44 relative to portion 46 can fracture and separate portion 44 from portion 46 at a predetermined force and/or torque limit, as described herein. In some embodiments, as force and/or torque is applied to portion 44 and resistance increases, for example, due to fixation of portion 44 with cavity 18, as described herein, the predetermined torque and force limit is approached. In some embodiments, portions 44, 46 include offset hex geometries.

In some embodiments, portions 44, 46 can fracture and separate at a predetermined force or torque limit, which may be in a range of approximately 20 Newton centimeters (N-cm) to 50 N-cm. In some embodiments, portions 44, 46 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of portions 44, 46.

Portion 46 includes a shaft 50 having an outer surface 52. Surface 52 includes a thread form 54 configured for engagement with surface 16. In some embodiments, thread form 54 is continuous along surface 52. In some embodiments, thread form 54 may include a single thread turn or a plurality of discrete threads. In some embodiments, other penetrating elements may be located on shaft 50, such as, for example, a nail configuration, barbs, expanding elements, raised elements, ribs, and/or spikes to facilitate engagement of shaft 50.

Cleat 42 includes a surface 60 that defines a cavity 62. Cavity 62 is configured for disposal of screw 40. Screw 40 is connected with cleat 42 by retention pin 64, as shown in FIG. 7. Retention pin 64 allow for rotation of screw 40 relative to cleat 42 to facilitate translation of cleat 42 into contact with tether 20 to engage and disengage cleat 42 with tether 20.

Cleat 42 includes a surface 66 oriented to engage tether 20 and/or transverse portion 38. Surface 66 is angled such that surface 66 is configured for alignment with transverse portion 38 to facilitate engagement of tether 20 in a locked orientation, as described herein. In some embodiments, surface 66 may include penetrating members, such as, for example, a plurality of teeth 68. In some embodiments, teeth 68 may have various configurations, for example, round, oval, rectangular, polygonal, irregular, tapered, offset, staggered, uniform and non-uniform. Cleat 42 is engageable with screw 40 such that as screw 40 is actuated, cleat 42 includes a range of translation within cavity 18 and slot 24 to facilitate engagement and/or disengagement with transverse portion 38 and/or tether 20 in a non-fixed and/or non-locking orientation with body 14 and a fixed and/or locked orientation with body 14. In the locked orientation, teeth 68 engage transverse portion 38 and/or tether 20 to fix tether 20 with body 14. Surface 66 engages transverse portion 38 to apply a compressive force and/or a friction force, as described herein, to fix tether 20 in a locked orientation.

Cleat 42 includes a surface 70. Surface 70 includes a protrusion, such as, for example, a flange 72. Flange 72 is configured for engagement with the surface that defines slot 24. Flange 72 slidably translates along slot 24 between ends 26, 30. Ends 26, 30 define a range of translation of flange 72 as flange 72 translates within slot 24. In some embodiments, flange 72 engages surface 28, which comprises a proximal stop corresponding to a translation limit for a non-locking orientation of locking element 22, as shown in FIG. 7. In some embodiments, flange 72 engages surface 32, which comprises a distal stop corresponding to a translation limit for a locking orientation of locking element 22, as shown in FIG. 9. Surfaces 28, 32 are configured to resist and/or prevent translation of flange 72 beyond a selected limit.

Figure 11:
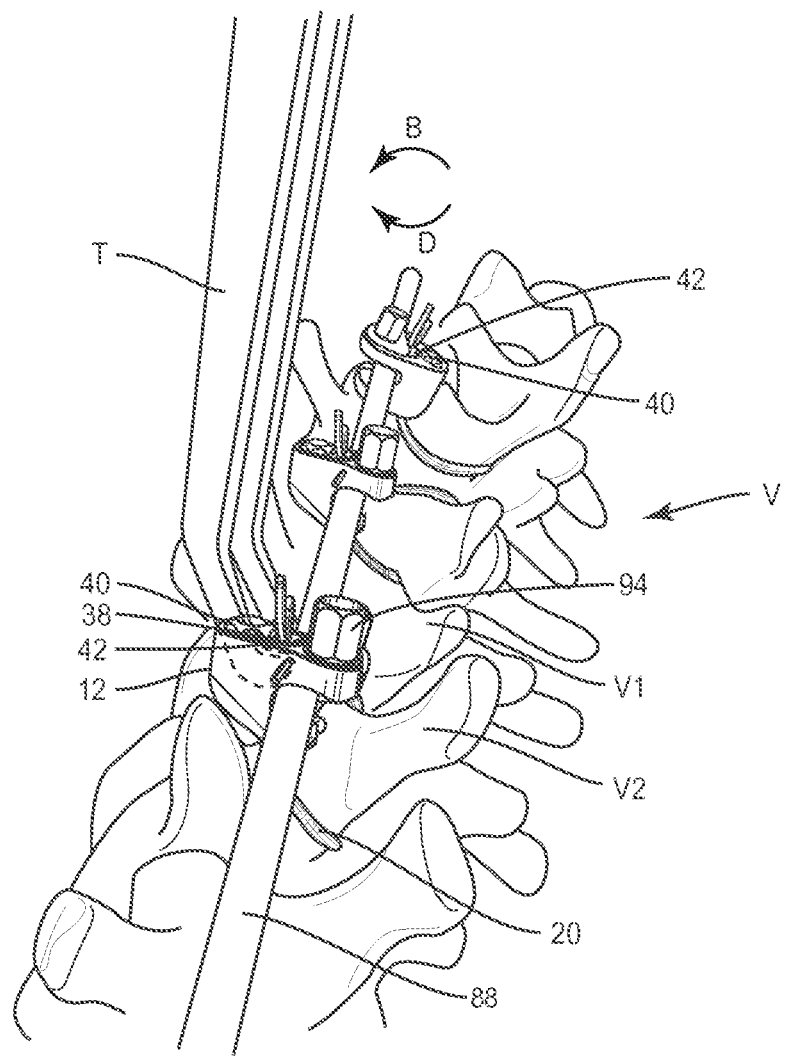
FIG. 11 is a perspective view of one embodiment of components of a surgical system in accordance with the principles of the present disclosure disposed with vertebrae.

Body 14 includes a wall 80 having a surface 82. Wall 80 includes extensions 84a, 84b. Extensions 84a, 84b define an opening, such as, for example, a bay 86 configured for disposal of a longitudinal element, such as, for example, a spinal rod 88 (FIG. 11). In some embodiments, cavity 18 is disposed separate and apart from bay 86. In some embodiments, cavity 18 is disposed transverse to bay 86. In some embodiments, cavity 18 may be disposed in various orientations, such as, for example, perpendicular, transverse and/or at angular orientations, such as acute or obtuse relative to bay 86. In some embodiments, cavity 18 may be disposed offset or staggered from bay 86. In some embodiments, bay 86 may have various cross section configurations, such as, for example, oval, oblong, triangular, rectangular, square, polygonal, irregular, uniform, non-uniform, variable and/or tapered. In some embodiments, surface 82 may include gripping elements or surfaces, such as, for example, rough, arcuate, undulating, mesh, porous, semi-porous, dimpled and/or textured to facilitate engagement with spinal rod 88.

Body 14 includes a surface 90 that defines a cavity, such as, for example, an opening 92. Surface 90 is threaded and configured for disposal of a coupling member, such as, for example, a set screw 94. In some embodiments, set screw 94 includes an end having a hexagonal geometry configured for engagement with a similarly shaped surgical tool, such as, for example, a driver. In some embodiments, set screw 94 includes an end having a cruciform, phillips, square, hexalobe, polygonal or star cross sectional configuration for disposal of a correspondingly shaped portion of a driver. Set screw 94 is configured for engagement with spinal rod 88 to facilitate fixation and/or locking of spinal rod 88 with body 14.

Set screw 94 is disposable between a non-locking orientation, such that spinal rod 88 is translatable relative to body 14 and a locked orientation, such that set screw 94 fixes spinal rod 88 with body 14. In some embodiments, set screw 94 includes a portion 102 and a portion 104. Portions 102, 104 are connected at a reduced diameter portion 106 that is frangibly connected to portion 104. In some embodiments, portions 102, 104 are fabricated from a fracturing and/or frangible material such that manipulation of portion 102 relative to portion 104 can fracture and separate portion 102 from portion 104 at a predetermined force and/or torque limit, as described herein.

In some embodiments, body 14 includes a mating surface 110 that defines cavities, such as, for example, mating capture elements 112 configured to mate with a surgical instrument to facilitate implant and manipulation of connector 12 and/or components of spinal implant system 10. In some embodiments, spinal implant system 10 may include one or a plurality of connectors 12 spaced apart and disposed along spinal rod 88, which may be relatively disposed in a side by side, irregular, uniform, non-uniform, offset and/or staggered orientation or arrangement, along one or a plurality of spinal rods 88. In some embodiments, spinal rod 88 extends along one or a plurality of vertebra, as described herein. In some embodiments, spinal implant system 10 may include one or a plurality of spinal rods 88, which may be relatively disposed in a side by side, irregular, uniform, non-uniform, offset and/or staggered orientation or arrangement.

Figure 10:
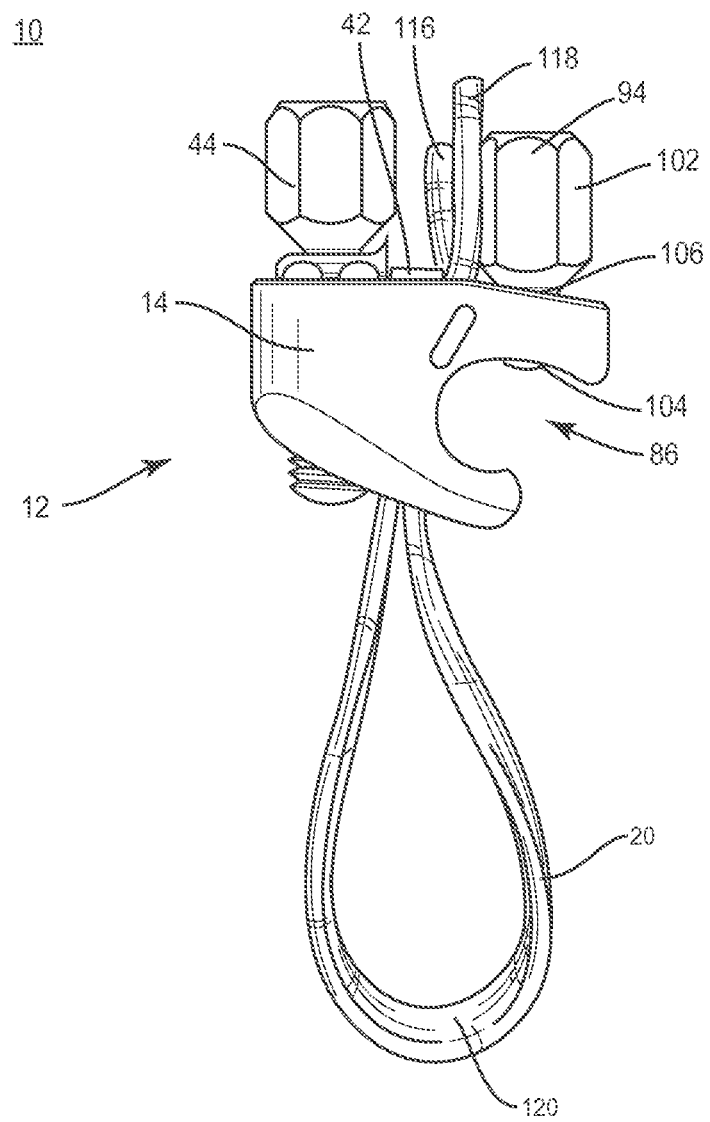
FIG. 10 is a side view of one embodiment of components of a surgical system in accordance with the principles of the present disclosure.

Tether 20 extends between an end 116 and an end 118, as shown in FIG. 10. Tether 20 is configured for engagement with connector 12, as described herein. In some embodiments, end 116 and end 118 form a loop 120 configured to surround all or a portion of tissue, such as, for example, laminae and/or spinal rod 88, as described herein. Tether 20 is configured for tensioning about a targeted portion of an anatomy of a body for attachment of tether 20 with the targeted portion of the anatomy, as described herein. In some embodiments, the targeted portion of the anatomy may include laminae, transverse process and/or pedicle regions of a vertebral level. In some embodiments, spinal implant system 10 may include one or a plurality of tethers 20, each tether 20 being configured for disposal about a single and separate vertebral level. In some embodiments, a single vertebral level may include one or a plurality of tethers 20.

Tether 20 has a flexible configuration and may be fabricated from materials, such as, for example, fabric, silicone, polyurethane, silicone-polyurethane copolymers, polymeric rubbers, polyolefin rubbers, elastomers, rubbers, thermoplastic elastomers, thermoset elastomers and elastomeric composites. In some embodiments, the flexibility of tether 20 includes movement in a lateral or side to side direction and prevents expanding and/or extension in an axial direction upon tensioning and attachment with a targeted portion of the anatomy. In some embodiments, all or only a portion of tether 20 may have a semi-rigid, rigid or elastic configuration, and/or have elastic properties, similar to the material examples described herein, such that tether 20 provides a selective amount of expansion and/or extension in an axial direction. In some embodiments, tether 20 may be compressible in an axial direction. Tether 20 can include a plurality of separately attachable or connectable portions or sections, such as bands or loops, or may be monolithically formed as a single continuous element.

Tether 20 can have a uniform thickness/diameter. In some embodiments, tether 20 may have various surface configurations, such as, for example, smooth and/or surface configurations to enhance fixation, such as, for example, rough, arcuate, undulating, porous, semi-porous, dimpled, polished and/or textured. In some embodiments, the thickness defined by tether 20 may be uniformly increasing or decreasing, or have alternate diameter dimensions along its length. In some embodiments, tether 20 may have various cross section configurations, such as, for example, oval, oblong, triangular, rectangular, square, polygonal, irregular, uniform, non-uniform, variable and/or tapered. In some embodiments, the surface of tether 20 may include engaging structures, such as, for example, barbs, raised elements and/or spikes to facilitate engagement with tissue of the targeted anatomy.

In some embodiments, the surface of tether 20 may include a pliable lead. In some embodiments, tether 20 may include a pliable lead such that tether 20 can be passed and/or guided through cavities of spinal tissue to resist and/or prevent non-desirable and/or harmful engagement with selected and/or sensitive anatomy of the spinal tissue. In some embodiments, the pliable lead is soft and flexible and configured to pass through a sub-laminar cavity of vertebrae without adhering to dura matter of a spinal cord and/or surfaces of a lamina of a vertebral level. In some embodiments, all or only a portion of the pliable lead is fabricated from a pliable, low-friction material, such as, for example, silicone, polyurethane, silicone-polyurethane copolymers, polymeric rubbers, polyolefin rubbers, elastomers, rubbers, thermoplastic elastomers, thermoset elastomers and elastomeric composites.

In some embodiments, tether 20 may have various lengths. In some embodiments, tether 20 may be braided, such as a rope, or include a plurality of elongated elements to provide a predetermined force resistance. In some embodiments, tether 20 may be made from autograft and/or allograft, and be configured for resorbable or degradable applications. In one embodiment, tether 20 is a cadaver tendon. In one embodiment, tether 20 is a tendon that may be harvested, for example, from a patient or donor. In some embodiments, a tendon harvested from a patient may be affixed in remote locations with the patient's body.

In assembly, operation and use, spinal implant system 10, similar to the systems and methods described herein, is employed with a surgical procedure, such as, for example, a correction treatment of an affected portion of a spine, for example, a correction treatment to treat adolescent idiopathic scoliosis and/or Scheuermann's kyphosis of a spine. In some embodiments, one or all of the components of spinal implant system 10 can be delivered or implanted as a pre-assembled device or can be assembled in situ. Spinal implant system 10 may be completely or partially revised, removed or replaced.

In use, to treat a selected section of vertebrae V, including vertebrae V1, V2, as shown in FIG. 11, a medical practitioner obtains access to a surgical site including vertebrae V in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of vertebrae V, as well as for aspiration and irrigation of a surgical region.

Tether 20 is delivered along the surgical pathway to a surgical site adjacent vertebrae V. End 116 of tether 20 is guided through channel 34 for attachment with connector 12, as described herein. Tether 20 is disposed with vertebrae V and threaded with channel 34, as described herein, to capture selected spinal tissue of vertebrae V, for example, tether 20 is wrapped about tissue of vertebra V1 and/or vertebra V2.

Screw 40 is rotated in a counter clockwise direction, as shown by arrow B in FIG. 11, to dispose in a non-locked orientation, as shown in FIG. 7, such that tether 20 is movable within channel 34 and cleat 42 is positioned such that flange 72 is engaged with surface 28. End 118 is inserted into channel 34 to form loop 120 about tissue of vertebra V1 and/or vertebra V2. In one embodiment, loop 120 is disposed about a transverse process of vertebra V2 by passing end 118 continuously about the transverse process. Loop 120 is fixed and/or attached with the transverse process and/or lamina. Tether 20 is threaded through channel 34.

A surgical instrument, such as, for example, a tensioner T is disposed adjacent connector 12. Tensioner T is aligned and engaged with mating capture elements 112 for releasable fixation and/or provisional fixation of tensioner T with connector 12. Tensioner T is actuated to tension tether 20 about vertebra V2. In some embodiments, the tension and/or tensile force applied to tether 20 and/or corrective forces applied to vertebrae V can be increased and/or decreased by tensioner T.

Screw 40 is actuated by a driver (not shown) by rotating screw 40 in a clockwise direction to engage cleat 42. Cleat 42 is translated within cavity 18, as shown by arrow C in FIG. 9. Translation of cleat 42 causes surface 66 and teeth 68 to engage tether 20 and/or transverse portion 38. Translation of cleat 42 causes flange 72 to approach and/or engage surface 32 of end 30 to dispose locking element 22 in a locked orientation with body 14. Surface 66 applies a compressive force and/or a friction force to the lock surface of transverse portion 38, as shown by arrow A in FIG. 9, to fix tether 20 in a locked orientation with body 14.

The driver is rotated in a clockwise direction, as shown by arrow D in FIG. 11, to a predetermined force and/or torque limit, to cause portions 44, 46 to separate, as described herein. This configuration fixes tension of tether 20 about vertebra V2 and tensions components of the spinal construct for attachment with vertebrae V and/or to apply corrective treatment to vertebrae V.

Spinal rod 88 is disposed with bay 86. Set screw 94 is engaged with opening 92. Set screw 94 is engaged with a surgical instrument, such as, for example, a driver (not shown), which advances set screw 94 into opening 92 in a non-locking orientation, as described herein. Spinal rod 88 is translatable relative to body 14. The driver engages set screw 94 to fix spinal rod 88 with body 14 and for attachment of spinal rod 88 with vertebrae V via tether 20.

In some embodiments, spinal implant system 10 includes a second spinal rod 88 (not shown) delivered along the surgical pathway to the surgical site adjacent a contra-lateral side of vertebrae V. Second spinal rod 88 is connected with the contra-lateral side of vertebrae V via one or more tethers 20, similar to spinal rod 88 described herein. In some embodiments, spinal rod 88 and second spinal rod 88 are fixed with vertebrae V in a side by side orientation and/or a bilateral arrangement to stabilize vertebrae V and affect growth for a correction treatment to treat spine pathologies, as described herein. In some embodiments, one or all of the components of spinal implant system 10 can be delivered or implanted as a pre-assembled device or can be assembled in situ, in a selected order of assembly or the order of assembly of the particular components of system 10 can be varied according to practitioner preference, patient anatomy or surgical procedure parameters. Spinal implant system 10 may be completely or partially revised, removed or replaced.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

In some embodiments, the components of spinal implant system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal implant system 10 may be used to prevent or minimize curve progression in individuals of various ages.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
    a body including opposite first and second surfaces and opposite top and bottom surfaces, the top and bottom surfaces extending from the first surface to the second surface, the body including an inner surface that defines a passageway that extends through the top and bottom surfaces, the body further including a bay that extends into the first surface; and
    a locking element comprising a screw and a fixation element, the screw being positioned within the passageway and including a non-threaded proximal portion and a threaded shank extending from the proximal portion, the proximal portion having a maximum diameter that is greater than a maximum diameter of the shank, the shank defining a longitudinal axis, the fixation element being coupled directly to the proximal portion such that the fixation element is translatable relative to the body along the longitudinal axis.

2. A spinal implant as recited in claim 1, wherein the fixation element is coupled to the screw by a pin.

3. A spinal implant as recited in claim 1, wherein the bay is positioned between the top surface and the bottom surface.

4. A spinal implant as recited in claim 1, wherein the body includes a channel that extends through the top and bottom surfaces, the channel comprising a first portion that is in communication with the passageway and a second section that is spaced apart from the passageway by a wall that defines a threaded portion of the inner surface.

5. A spinal implant as recited in claim 4, wherein the threaded shank directly engages the threaded portion.

6. A spinal implant as recited in claim 4, wherein the body includes a second inner surface that defines a portion of the channel, the second inner surface including a portion that extends transverse to the longitudinal axis and is configured for engagement with the fixation element.

7. A spinal implant as recited in claim 1, wherein the body includes an opening that extends through the top surface, the opening being in communication with the bay.

8. A spinal implant as recited in claim 7, wherein the opening extends transverse to the longitudinal axis.

9. A spinal implant as recited in claim 7, wherein the opening is threaded.

10. A spinal implant as recited in claim 1, wherein the bottom surface is permanently fixed relative to the top surface.

11. A spinal implant as recited in claim 1, wherein the inner surface further defines a slot having a proximal end and a distal end, the fixation element being engageable with the inner surface adjacent to the ends to define a range of translation of the locking element within the cavity.

12. A spinal implant as recited in claim 11, wherein the fixation element includes an outer flange that is engageable with the inner surface adjacent to the ends.

13. A spinal implant as recited in claim 1, wherein the fixation element surrounds a portion of the shank.

14. A spinal implant as recited in claim 1, wherein the proximal portion defines a socket configured for disposal of a bit of a driver.

15. A spinal implant comprising:
    a body including opposite first and second surfaces and opposite top and bottom surfaces, the top and bottom surfaces extending from the first surface to the second surface, the bottom surface being permanently fixed relative to the top surface, the body including an inner surface that defines a passageway that extends through the top and bottom surfaces, the body further including a bay that extends into the first surface, the bay being spaced apart from the passageway by the inner surface; and
    a locking element comprising a screw and a fixation element, the screw being positioned within the passageway and including a non-threaded proximal portion and a threaded shank extending from the proximal portion, the proximal portion having a maximum diameter that is greater than a maximum diameter of the shank, the shank defining a longitudinal axis, the shank comprising a thread that directly engages a threaded portion of the inner surface, the fixation element being coupled directly to the proximal portion such that the fixation element is translatable relative to the body along the longitudinal axis.

16. A spinal implant as recited in claim 15, wherein the body includes a channel that extends through the top and bottom surfaces, the channel comprising a first portion that is in communication with the passageway and a second section that is spaced apart from the passageway by a wall that defines a threaded portion of the inner surface.

17. A spinal implant as recited in claim 16, wherein the body includes a second inner surface that defines a portion of the channel, the second inner surface including a portion that extends transverse to the longitudinal axis and is configured for engagement with the fixation element.

18. A spinal implant as recited in claim 15, wherein the body includes an opening that extends through the top surface, the opening being in communication with the bay.

19. A spinal implant as recited in claim 18, wherein the opening is threaded and extends transverse to the longitudinal axis.

20. A spinal implant comprising:

a body including opposite first and second surfaces and opposite top and bottom surfaces, the top and bottom surfaces extending from the first surface to the second surface, the bottom surface being permanently fixed relative to the top surface, the body including an inner surface that defines a passageway that extends through the top and bottom surfaces, the body further including a bay that extends into the first surface, the bay being spaced apart from the passageway by the inner surface, the body including a channel that extends through the top and bottom surfaces, the channel comprising a first portion that is in communication with the passageway and a second section that is spaced apart from the passageway by a wall that defines a threaded portion of the inner surface; and a locking element comprising a screw and a fixation element, the screw being positioned within the passageway and including a non-threaded proximal portion and a threaded shank extending from the proximal portion, the proximal portion having a maximum diameter that is greater than a maximum diameter of the shank, the shank defining a longitudinal axis, the shank comprising a thread that directly engages a threaded portion of the inner surface, the fixation element being coupled directly to the proximal portion such that the fixation element is translatable relative to the body along the longitudinal axis, wherein the body includes a second inner surface that defines a portion of the channel, the second inner surface including a portion that extends transverse to the longitudinal axis and is configured for engagement with the fixation element, and wherein the body includes an opening that extends through the top surface, the opening being in communication with the bay, the opening being threaded and extending transverse to the longitudinal axis.

* * * * *